(12) United States Patent
Hauger et al.

(10) Patent No.: US 10,054,775 B2
(45) Date of Patent: Aug. 21, 2018

(54) OPTICAL SYSTEM FOR FLUORESCENCE OBSERVATION

(71) Applicant: Carl Zeiss Meditec AG, Jena (DE)

(72) Inventors: Christoph Hauger, Aalen (DE); Roland Guckler, Ulm (DE)

(73) Assignee: CARL ZEISS MEDITEC AG, Jena (DE)

( * ) Notice: Subject to any disclaimer, the term of this patent is extended or adjusted under 35 U.S.C. 154(b) by 334 days.

(21) Appl. No.: 14/940,639

(22) Filed: Nov. 13, 2015

(65) Prior Publication Data

US 2016/0139391 A1    May 19, 2016

(30) Foreign Application Priority Data

Nov. 13, 2014 (DE) .................. 10 2014 016 850

(51) Int. Cl.
*G02B 21/00*    (2006.01)
*A61B 5/00*    (2006.01)
(Continued)

(52) U.S. Cl.
CPC ........ *G02B 21/0012* (2013.01); *A61B 5/0071* (2013.01); *G02B 21/16* (2013.01);
(Continued)

(58) Field of Classification Search
CPC .................. G01N 21/6458; G01N 21/6486
See application file for complete search history.

(56) References Cited

U.S. PATENT DOCUMENTS

| 5,127,730 A | 7/1992 | Brelje et al. |
| 5,166,813 A | 11/1992 | Metz |
| (Continued) | | |

FOREIGN PATENT DOCUMENTS

| DE | 195 48 913 A1 | 7/1997 |
| DE | 691 31 176 T2 | 12/1999 |
| (Continued) | | |

OTHER PUBLICATIONS

Office Action in corresponding German Application No. 10 2014 016 850.6 dated Aug. 18, 2015.

*Primary Examiner* — David Porta
*Assistant Examiner* — Djura Malevic
(74) *Attorney, Agent, or Firm* — Patent Portfolio Builders PLLC

(57) ABSTRACT

An optical system for fluorescence observation comprises optics including an ocular 17, a camera 55, a display 69, a light source 71, an illumination light filter 84, an observation light filter 57 and a controller 35. The observation filter has multiple transmitting regions which allows light which was generated by a fluorescence to traverse for observation. The transmitting ranges are divided by blocking ranges. At the wavelength ranges at which the observation filter has a transmitting region the illumination filter has a blocking region and the other way round. The multiple transmitting regions of the illumination filter enable an improved color impression under normal light observation. The controller is configured to process a fluorescent light image obtained by the camera by identifying a contiguous fluorescent region in the fluorescent light image, generating an image including a representation of the boundary of the contiguous fluorescent region, and supplying the generated image to the display.

7 Claims, 6 Drawing Sheets

(51) Int. Cl.
*G02B 21/16* (2006.01)
*G02B 21/18* (2006.01)
*G02B 21/22* (2006.01)
*G02B 5/28* (2006.01)

(52) U.S. Cl.
CPC ............ *G02B 21/18* (2013.01); *G02B 21/22* (2013.01); *G02B 5/28* (2013.01)

(56) References Cited

U.S. PATENT DOCUMENTS

| | | | | |
|---|---|---|---|---|
| 5,512,940 | A * | 4/1996 | Takasugi | G06T 7/0012 348/30 |
| 5,719,024 | A | 2/1998 | Cabib et al. | |
| 5,799,682 | A | 9/1998 | Affleck et al. | |
| 5,817,462 | A | 10/1998 | Garini et al. | |
| 6,212,425 | B1 * | 4/2001 | Irion | A61B 1/00186 600/476 |
| 6,899,675 | B2 * | 5/2005 | Cline | A61B 1/00009 600/109 |
| 7,485,878 | B2 * | 2/2009 | Weiss | G01N 1/286 250/486.1 |
| 2001/0046673 | A1 * | 11/2001 | French | C12Q 1/6827 435/6.11 |
| 2002/0020800 | A1 * | 2/2002 | Knebel | G02B 21/0028 250/201.3 |
| 2003/0011772 | A1 * | 1/2003 | Abe | G01N 21/6458 356/417 |
| 2003/0197119 | A1 * | 10/2003 | Engelhardt | G02B 21/002 250/234 |
| 2003/0206296 | A1 * | 11/2003 | Wolleschensky | G02B 21/0016 356/317 |
| 2004/0027683 | A1 * | 2/2004 | Dietzsch | G02B 21/0088 359/655 |
| 2004/0084426 | A1 * | 5/2004 | Okada | B23K 26/032 219/121.68 |
| 2004/0095576 | A1 * | 5/2004 | Wolleschensky | G01N 21/6428 356/317 |
| 2004/0109231 | A1 | 6/2004 | Haisch et al. | |
| 2004/0114219 | A1 | 6/2004 | Richardson | |
| 2004/0252379 | A1 * | 12/2004 | Weiss | G02B 5/003 359/629 |
| 2005/0010081 | A1 * | 1/2005 | Doguchi | A61B 1/00009 600/109 |
| 2005/0024721 | A1 * | 2/2005 | Storz | G02B 21/002 359/385 |
| 2005/0103973 | A1 * | 5/2005 | Abe | G01N 21/6458 250/201.3 |
| 2006/0007548 | A1 * | 1/2006 | Watanabe | G02B 5/28 359/589 |
| 2006/0179992 | A1 * | 8/2006 | Kermani | G01N 1/06 83/651 |
| 2006/0186349 | A1 * | 8/2006 | Weiss | G01N 1/286 250/486.1 |
| 2007/0051869 | A1 * | 3/2007 | Knebel | G02B 21/0032 250/201.3 |
| 2007/0058246 | A1 | 3/2007 | Westphal et al. | |
| 2007/0090985 | A1 * | 4/2007 | Jess | G01N 21/6428 341/155 |
| 2009/0202119 | A1 | 8/2009 | Hefti et al. | |
| 2010/0044583 | A1 * | 2/2010 | Steffen | A61B 5/0059 250/458.1 |
| 2011/0149084 | A1 * | 6/2011 | Beck | A61B 1/00057 348/187 |
| 2012/0057226 | A1 * | 3/2012 | Kuster | G02B 21/0012 359/376 |
| 2012/0300294 | A1 * | 11/2012 | Jess | G01J 3/0235 359/385 |
| 2013/0307953 | A1 | 11/2013 | Hauger et al. | |
| 2015/0346098 | A1 | 12/2015 | Hauger et al. | |

FOREIGN PATENT DOCUMENTS

| | | |
|---|---|---|
| DE | 297 24 412 U1 | 3/2001 |
| DE | 103 39 784 A1 | 3/2004 |
| DE | 10 2011 002 990 A1 | 7/2012 |
| DE | 10 2014 008 243 A1 | 12/2015 |
| EP | 2 074 933 A1 | 11/2008 |
| JP | 2005-121479 A | 5/2005 |
| WO | 2004/090604 A2 | 10/2004 |

* cited by examiner

OPTICAL SYSTEM FOR FLUORESCENCE OBSERVATION

CROSS-REFERENCES TO RELATED APPLICATIONS

The present application claims priority of Patent Application No. 10 2014 016 850.6, filed Nov. 13, 2014 in Germany, the entire contents of which are incorporated by reference herein.

FIELD

The present invention relates to an optical system, in particular a surgical microscope for observing a fluorescence and in particular for observing a fluorescence of Protoporphyrine IX.

BACKGROUND

Fluorescence is used in medical practice for visualizing certain types of tissue. For this purpose, substances are administered to a patient which selectively accumulate in different types of tissue and provide fluorescent substances in these tissues. When illuminated with suitable light, a fluorescence of the fluorescent substances will be excited, and it is possible to observe the emitted fluorescent light. In an image recorded with the fluorescent light, certain tissues having a higher concentration of the fluorescent substance appear brighter than surrounding tissues containing lower concentrations of the fluorescent substances. For example, when the administered substance concentrates in the a certain tumor tissue, tissue regions affected by the tumor can be visualized and differentiated from the surrounding tissue regions not affected by the tumor.

Treatments to the human body can be performed by using surgical microscopes allowing to perform fluorescence observation. Such surgical microscope typically includes an illumination light filter in a beam path between a light source and an observed object, and an observation light filter in a beam path between the object and an observing eye or a camera detecting images of the object. The illumination light filter allows light having wavelengths suitable for exciting a fluorescence in the object to traverse the filter and to reach the object. The observation light filter allows fluorescent light emanating from the object to traverse the filter and reach the observing eye or camera. The illumination light filter is further configured to block light having wavelengths of the fluorescent light which can traverse the observation light filter, so that substantially only light generated by the fluorescence traverses the observation light filter while illumination light reflected or scattered at the object does not reach the observing eye or camera. The illumination light filter blocks a significant amount of the spectrum of the illumination light so that, if the used light source is a white light source, the illumination light reflected or scattered at the object will not allow to perceive the object with a natural unaltered color impression.

An example of a substance to visualize certain types of tumors is Protoporphyrine IX which is selectively accumulated in tumor tissues by administering 5-Aminoluvelinacid (5-ALA) to the patient.

Protoporphyrine IX is also used for visualizing tumors of the human brain. Herein, it is important for the surgeon to be able to accurately identify the boundary of a tumor in order to remove the tumor without removing surrounding tissues, so that important functions of the brain are preserved.

From U.S. Pat. No. 6,212,425 B1 there is known an optical filter system including an illumination light filter and an observation light filter adapted to allow observation of the fluorescence of Protoporphyrine IX.

When using this light filter system, the healthy tissue is visible in a blue color, tumor tissue is visible in a red color, and boundary regions of the tumor tissue appears in a mixed color, which is described by many people as salmon colored, so that it is relatively easy to identify the boundary of the tumor tissue. However there is a problem, in that details of the healthy tissue, such as blood vessels are not visible since the healthy tissue is only visible as a blue tissue. In order to identify such details of the healthy and/or tumor tissue, it is conventionally necessary for the surgeon to switch from a fluorescence observation mode of the surgical microscope to a normal light observation mode, in which details of the healthy tissue and the tumor tissue are visible while it is not possible to distinguish between the healthy and the tumor tissue. The switching back and forth between the fluorescence observation mode and the normal light observation mode is very demanding for the surgeon.

Thus, it is desirable to be able to visualize the fluorescence of fluorescent regions and to perceive a relatively unaltered natural color impression of the non-fluorescent regions in a same mode of the surgical microscope.

SUMMARY

Thus, it is an object of the present invention to provide an optical system for fluorescence observation, which allows to observe non-fluorescent regions in a substantially unaltered color impression.

According to embodiments of the invention, an optical system for fluorescence observation comprises optics including an ocular, a camera, a display, a light source, a first illumination light filter, a first observation light filter and a controller. The optics provide a first beam path from the light source to an object region for illuminating the object region, a second beam path from the object region to the ocular for imaging the object region via the ocular, a third beam path from the object region to the camera for imaging the object region onto the camera, and a fourth beam path from the display to the ocular for displaying an image displayed by the display via the ocular. The optical system has a first mode of operation in which the first illumination light filter is arranged in the first beam path and in which the first observation light filter is arranged in the third beam path.

According to exemplary embodiments, the first illumination light filter and the first observation light filter are adapted to each other. The first observation light filter has plural transmitting regions provided for allowing light generated by a fluorescence to traverse the filter for observation or detection of the fluorescence. The transmitting regions do not overlap, i.e. they are separated by blocking regions, which substantially do not allow light of the respective wavelengths to traverse the filter. Transmitting regions and blocking regions differ from each other in the transmittance for light of a given wavelength. At a given wavelength, the transmittance of a transmitting region is significantly greater than the transmittance of a blocking region. Within a blocking region, or a transmitting region, the transmittance is not required to be constant. In order characterize the transmittance of a blocking region or a transmitting region, it is possible to refer to a mean transmittance of that region, for example. The mean transmittance of a blocking or transmitting region can be determined by measuring the transmittance at plural wavelengths within a wavelength range corresponding to the respective and by averaging the plural measurements.

The first observation light filter has a transmitting region at those wavelengths at which the first illumination light filter has a blocking region, so that the object, being illuminated through the first illumination light filter, does not reflect or scatter light which could traverse one of the transmitting regions of the first observation light filter. The light, which can traverse the transmitting regions of the first observation light filter is then mainly fluorescent light generated by a fluorescence of the object. The first illumination light filter has transmitting regions allowing light having wavelengths suitable to excite the fluorescence to traverse the first illumination light filter.

According to exemplary embodiments, the first observation light filter has blocking regions at such wavelengths at which the first illumination light filter has transmitting regions.

According to further exemplary embodiments, the following relation is fulfilled in a wavelength range from 380 nm to 725 nm:

$$\frac{1}{345 \text{ nm}} \int_{380 nm}^{725 nm} T^O(\lambda) \cdot T^I(\gamma) \, d\lambda < 0.01,$$

wherein $T^O(\lambda)$ is the transmittance of the first observation light filter in dependence of the wavelength $\lambda$ and $T^I(\lambda)$ is the transmittance of the first illumination light filter in dependence on the wavelength $\lambda$.

The above formula indicates that light of a wavelength $\lambda$ from this wavelength range can substantially not traverse both the illumination light filter and the observation light filter.

In a fluorescence observation of an object, the object can be illuminated through the first illumination light filter, and a fluorescence of the object can be observed and detected with light which has traversed the first observation light filter. It is further possible to directly observe the object and to detect the light emanating from the object and having not traversed the first observation light filter. This observation can be performed, for example, directly by the eye, without using any additional optics. This observation can be also performed with additional optics, such as an ocular of a surgical microscope into which the surgeon can look in order to see the object. The optics can be configured to image the object onto a camera to detect images of the object. Such observation or detection of light having not traversed the observation light filter is substantially independent of fluorescence processes occurring in the object. The light seen by the eye or detected by the camera is light which has traversed the illumination light filter and which has subsequently been reflected or scattered at the object. If the object were illuminated with light which has not traversed the illumination light filter, the object would appear in its natural colors for direct observation or detection with a camera. When the object is illuminated with light which has traversed the first illumination light filter, the object is not illuminated with light of having wavelengths from within wavelength ranges at which the first illumination light filter has blocking regions. Thus, the object is not illuminated with white light, but with light which includes plural wavelengths of the visible light from which certain wavelength ranges are missing, so that a natural unaltered color impression of the object will probably not occur.

For that reason, the first observation light filter does not comprise one single transmitting region allowing to detect the fluorescence, but plural non-overlapping transmitting regions, which are separated by respective blocking regions of the first observation light filter. At wavelengths where the first observation light filter has a blocking region, the first illumination light filter may have a transmitting region to illuminate the object with light having wavelengths suitable or not suitable for exciting the fluorescence. Due to the blocking region of the first observation light filter such light does not contribute to the detected fluorescence. Therefore, such light merely illuminates the object and can, by suitably selecting the blocking regions arranged between transmitting regions, contribute to adjust the distribution of wavelengths of the illuminating light such that the object appears in its natural color when the observation is performed without using the first observation light filter. Thus, "gaps" in the illumination light filter are partially "filled". This provides the advantage that the color impression, caused by the object during observation without use of the observation light filter, can be improved. By this, generated fluorescent light having wavelengths from within the blocking regions of the first observation light filter will not be detected. This may have a disadvantage that the contrast of a fluorescent light image can be decreased since of not all the available fluorescent light is detected. However, by suitably selecting the blocking regions arranged between the transmitting regions of the first observation light filter the significant advantage is achieved that the natural color impression of the object is substantially improved when the object is illuminated with light having traversed the first illumination light filter.

According to exemplary embodiments, the illumination light filter has, in the wavelength range between 440 nm and 560 nm, a wavelength range which has a width greater than 45 nm and in which the transmittance of the first illumination light filter is smaller than 0.80. This reduces the amount of green light reaching the object and results in a further improvement of the color impression under normal light observation.

According to exemplary embodiments, the wavelength range in which the transmittance is smaller than 0.80 is provided in a region between 465 nm and 540 nm. According to further exemplary embodiments herein, the wavelength range has a width greater than 45 nm and the transmittance is smaller than 0.70 and, in particular, smaller than 0.65 in that wavelength range.

According to exemplary embodiments, the optical system for fluorescence observation comprises an illumination light filter and an observation light filter, wherein the observation light filter has, in a wavelength range from 380 nm to 725 nm, the following transmission characteristics: at least two non-overlapping transmitting regions of the first observation light filter, each of the transmitting regions having, between a first wavelength and a second wavelength, a mean transmittance greater than a first value; and plural blocking regions of the first observation light filter, wherein a number of the blocking regions is equal to the number of the transmitting regions of the observation light filter, wherein the plural blocking regions include a first blocking region of the observation light filter having, between 380 nm and a smallest one of the first wavelengths of the at least two transmitting regions of the observation light filter, a mean transmittance smaller than a second value, and at least one further blocking region of the first observation light filter, each of the further blocking regions having, between the second wavelength of one of the at least two transmitting regions of the observation light filter and the first wavelength of a further one of the at least two transmitting regions of the first observation light filter, a mean transmittance smaller than a third value.

The first illumination light filter has, in a wavelength range from 380 nm to 725 nm, a transmission characteristics as follows: plural transmitting regions of the first illumination light filter, the plural transmitting regions including a first transmitting region of the first illumination light filter having, between 380 nm and a wavelength smaller than the smallest of the first wavelengths of the at least two transmitting regions of the first observation light filter, a mean transmittance greater than a fourth value; and further transmitting regions of the first illumination light filter, each of the further transmitting regions having, between a wavelength greater than the second wavelength of a transmitting region of the first observation light filter and a wavelength smaller than the first wavelength of a further transmitting region of the observation light filter, a transmittance greater than a fifth value, and plural blocking regions of the first illumination light filter, each of the blocking regions of the first illumination light filter having, between the wavelength smaller than the first wavelength of one of the transmitting regions of the first observation light filter, and the wavelength greater than the second wavelength of this transmitting region of the first observation light filter, a mean transmittance smaller than a sixth value.

The detection of a fluorescence using an observation light filter having plural transmitting regions which are separated by corresponding blocking regions is suitable for the detection of a fluorescence having a broad emission spectrum. A broad emission spectrum is an emission spectrum having significant intensities of the fluorescence emission in a relatively broad wavelength range. A broad emission spectrum may have, for example, intensities greater than 10% of a maximum intensity of the fluorescence spectrum in a wavelength range having a width of more than 50 nm, or more than 100 nm. In order to detect the fluorescence, such broad fluorescence spectrum can be divided into plural regions using the observation light filter, wherein the blocking region, between two transmitting regions, allows illumination of the object with light improving the natural color impression for direct observation. Herein, it is possible to provide two, three or more transmitting regions in the observation light filter, wherein two adjacent transmitting regions are separated by corresponding blocking regions. At the wavelengths which are included in one blocking region of the observation light filter, the corresponding illumination light filter has transmitting regions which improve the natural color impression.

An example of a fluorescence for which the illumination light filter and observation light filter illustrated above can be advantageously used is the fluorescence of Protoporphyrine IX. This fluorescence is used for visualizing tumors. This application appears to be particularly promising for visualizing high-grade and low-grade gliomas since no conventional methods are known for visualizing low-grade gliomas.

According to exemplary embodiments, the controller is configured to process a fluorescence image obtained by a camera in the first mode of operation, by identifying a contiguous fluorescent region in the fluorescence image based on at least one decision parameter, to generate a representation of the boundary of the contiguous fluorescent region, and generating an image, including the representation of the boundary of the contiguous fluorescent region, and to transmit the generated image to the display for presentation.

In the first mode of operation, the first observation light filter can be arranged in the third beam path between the object region and the camera, so that the camera detects a fluorescence image of the object region. The first observation light filter can also be arranged in the second beam path between the object region and the ocular. If the first observation light filter is not arranged in the second beam path, the observer using the ocular is able to observe the object, as illustrated above, with a nearly unaltered natural color impression. The controller can perform image processing of the fluorescence image obtained by the camera and generate an image which is transmitted to the display for presentation. The image displayed on the display is also visible in the ocular via the fourth beam path. In the ocular, the displayed image can be shown in superposition with the image of the object region projected into the ocular via the first beam path. The controller may generate the image such, that it represents the fluorescent structures or structures derived from fluorescent structures. These fluorescent structures or structures derived from fluorescent structures can be observed by the observer via the ocular in superposition with the normal light image of the object region. The fluorescent structures or structures derived from fluorescent structures can be represented within the image using a designated color. For example, the color green can be used for this purpose.

The generated image is generated by image processing based on the detected fluorescent light image. Herein, it has to be decided for a plurality of locations of the generated image, for example for each pixel of the image, whether the generated image should contain a color, so that the image information of the generated image is superimposed with the normal light image, or whether the generated image should contain no color and be transparent at these locations or pixels, so that corresponding locations of the normal light image are not superimposed with image information of the generated image. The image processing may identify contiguous fluorescent regions in the fluorescence image. Herein, it has to be decided whether a particular location, or pixel, of the fluorescent light image is a location of a fluorescent region or not. Such decision can be based on at least one decision parameter. The decision parameter may be, for example, a threshold for an intensity at a location of the fluorescent light image. Based on a comparison of an intensity at a given location or pixel of the fluorescent light image with the threshold, it can be decided whether the given location or pixel, respectively, of the fluorescent light image corresponds to a fluorescent region of the object. If the intensity of the location or pixel of the fluorescence image exceeds the threshold, the location or the pixel is within the fluorescent region. Conversely, the location or pixel of the fluorescence image is not within the fluorescent region when the intensity of the fluorescence image at this location or pixel is smaller than the threshold. Other decision parameters are conceivable.

The identified contiguous fluorescent regions can be represented in the generated image. This in particular is possible because the representation of the boundaries of the contiguous fluorescent regions are contained in the generated image. The boundary of the fluorescent region can be represented, for example, by a line contained in the generated image, wherein the line extends along the boundary of the fluorescent region. A user looking into the ocular will then see lines which are superimposed with the normal light image, wherein the lines indicate the boundaries of the fluorescent regions. If the fluorescence is caused by a fluorescent substance which concentrates in a tumor tissue, then the lines indicate and visualize the boundaries of the tumor tissue in the normal light image and simplify the removal of the tumor tissue, so that the tumor tissue can be removed entirely without removing too much of the surrounding healthy tissue.

According to exemplary embodiments, the optical system comprises an input device to modify or to edit the at least one decision parameter.

According to exemplary embodiments, the optics further comprises a second illumination light filter and a second observation light filter, wherein the optical system has a second mode of operation, in which the second illumination light filter is arranged in the first beam path and the second observation light filter is arranged in the third beam path while the first illumination light filter and the first observation light filter are removed from their positions in the beam paths.

The second illumination light filter and the second observation light filter are arranged in the beam paths in the second mode of operation instead of the first illumination light filter and the first observation light filter. They are adapted to the observation of the fluorescence of the same fluorescent substance as the first illumination light filter and the first observation light filter. However the second illumination light filter and the second observation light filter have transmitting regions and blocking regions different from the transmitting regions and blocking regions of the first illumination light filter and the first observation light filter. Thus, the second observation light filter provides an alternative to the first observation light filter for the observation of the same fluorescence. This can be helpful for verifying the structure of the fluorescent regions and/or boundaries of the fluorescent regions identified in the first mode of operation. This can also be helpful if it is desired to verify that the image processing of the fluorescent light image is performed by the controller as intended. In particular, the second mode of operation can also be used to adjust the decision parameter used in the image processing in the first mode of operation. The image processing in the first mode of operation can be calibrated based on the fluorescent light images obtained in the second mode of operation, accordingly. In particular a fluorescent light image generated in the second mode of operation can be processed by identifying the boundaries of contiguous fluorescent regions. The optical system can then be switched to the first mode of operation to generate a fluorescent light image of the same object region in the first mode of operation. The image processing illustrated above using the at least one decision parameter can be applied to the fluorescent light image obtained in the first mode of operation. When identified boundaries of the fluorescent regions in the generated image coincide with the boundaries of the fluorescent regions identified in the fluorescence image obtained in the second mode of operation, it can be assumed that the at least one decision parameter is correctly set. If this is not the case, the at least one decision parameter can be varied until the boundaries of the fluorescent regions identified in the fluorescent light image generated in the first mode of operation substantially coincide with the boundaries of the fluorescent regions identified in the fluorescent light image which was generated during the second mode of operation.

According to exemplary embodiments the second illumination light filter has, in a wavelength range from 380 nm to 725 nm, transmission characteristics as follows: a transmitting region of the second illumination light filter having, between 380 nm and a first wavelength smaller than the smallest of the wavelengths of the at least two transmitting regions of the first observation light filter, a mean transmittance greater than the fourth value; and a blocking region of the second illumination light filter having, between a second wavelength greater than the first wavelength and smaller than the smallest of the wavelengths of the at least two transmitting regions of the first observation light filter, and 725 nm, a mean transmittance smaller than the sixth value. The second observation light filter has, in a wavelength range from 380 nm to 725 nm, transmission characteristics as follows: a blocking region of the second observation light filter having, between 380 nm and the first wavelength, a mean transmittance smaller than the second value; and a transmitting region of the second observation light filter having, between the second wavelength and 725 nm, a mean transmittance greater than the first value. The following formula $T^{O2}(\lambda) \cdot T^{I2}(\lambda) \geq 0.05$ is fulfilled in only one wavelength range while the following formula $T^{O2}(\lambda) \cdot T^{I2}(\lambda) < 0.05$ is fulfilled for all other wavelengths outside of this one wavelength range. $T^{O2}(\lambda)$ is the transmittance of the second observation light filter in dependence of the wavelength $\lambda$, and $T^{I2}(\lambda)$ is the transmittance of the second illumination light filter in dependence of the wavelength $\lambda$. The wavelength range extends between the first wavelength and the second wavelength, and the wavelength range extends over more than 50 nm.

With such configuration of the second illumination light filter and the second observation light filter, not only fluorescent light reaches the camera but also illumination light from the wavelength range in which the product of the transmittance of the second illumination light filter and the transmittance of the second observation light filter is greater than 0.05. This illumination light which reaches the camera has wavelengths which are substantially different from the wavelengths of the fluorescent light reaching the camera, so that the illumination light and the fluorescent light have different colors.

According to exemplary embodiments, the camera is a color camera and the controller is configured to process the fluorescent light images obtained in the second mode of operation, by identifying boundaries of the fluorescent regions based on color information of the fluorescent light image obtained in the second mode of operation. At the boundaries of the fluorescent regions there is a color transition from the color of the fluorescent light in the interior of the fluorescent region to the color of the illumination light which traverses the second illumination light filter and the second observation light filter in the 50 nm wide wavelength range. This color transition can be seen by the eye of the observer, and it can be also detected by an image analysis of the color information of the fluorescent light image obtained in the second mode of operation. Boundaries of fluorescent regions in the fluorescent light image obtained in the second mode of operation can be identified based on the locations of these color transitions in the image. These identified fluorescent regions can then be used to adjust the at least one decision parameter which is used in the image processing of the fluorescent light image obtained in the first mode of operation. When the second illumination light filter and the second observation light filter are adapted to observe the fluorescence of Protoporphyrine IX, non-fluorescent regions appear blue in the fluorescent light image obtained in the second mode of operation and fluorescent regions appear red in this fluorescent light image, and the color transition at the boundaries of the fluorescent regions appear salmon colored.

BRIEF DESCRIPTION OF THE DRAWINGS

The forgoing as well as other advantageous features of the disclosure will be more apparent from the following detailed description of exemplary embodiments with reference to the accompanying drawings. It is noted that not all possible embodiments necessarily exhibit each and every, or any, of the advantages identified herein.

DETAILED DESCRIPTION OF EXEMPLARY EMBODIMENTS

Figure 1:
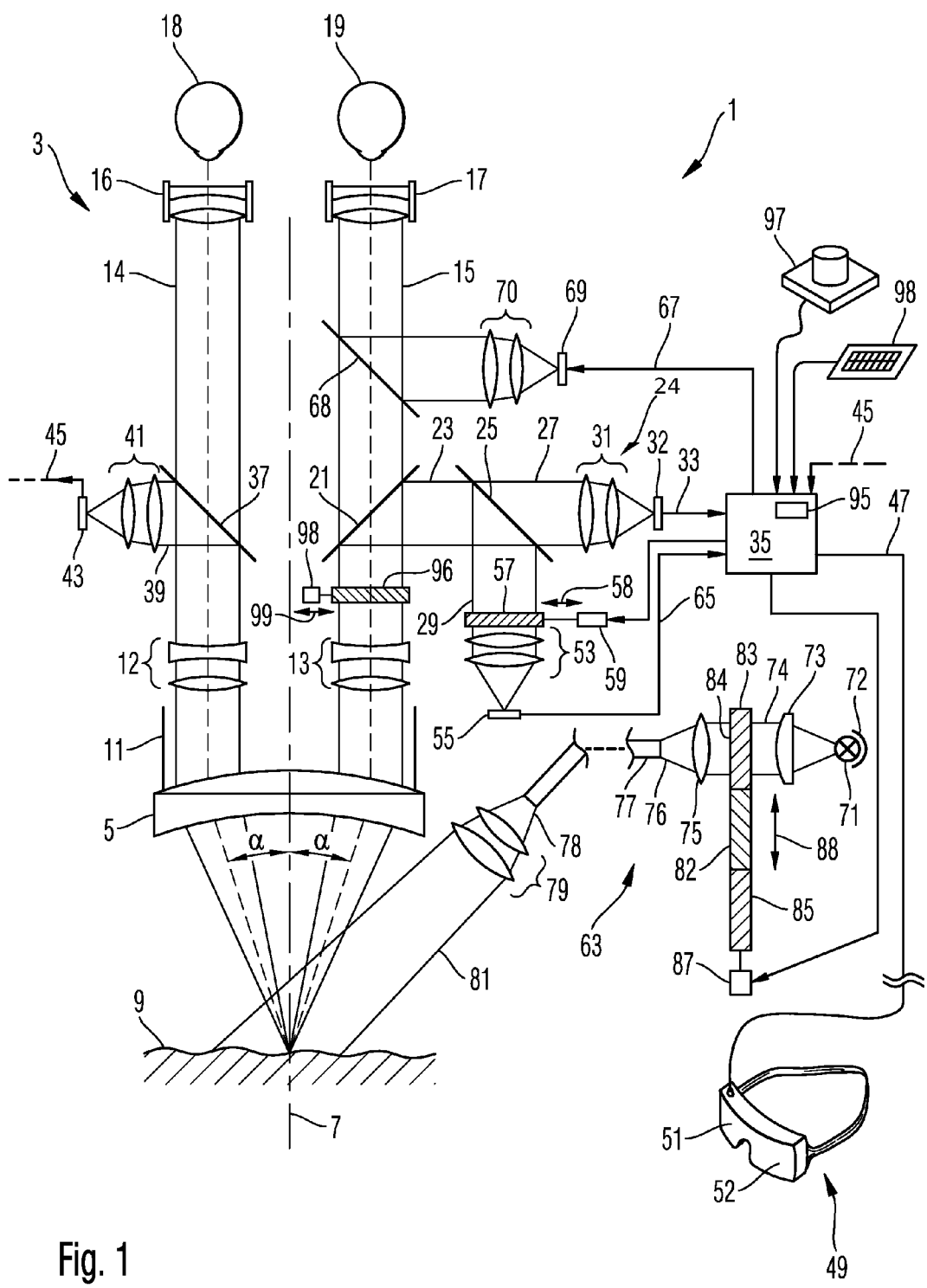
FIG. 1 is a schematic illustration of an embodiment of an optical system for fluorescence observation.

In the exemplary embodiments described below, components that are alike in function and structure are designated as far as possible by alike reference numerals. Therefore, to understand the features of the individual components of a specific embodiment, the descriptions of other embodiments and of the summary of the disclosure should be referred to.

A surgical microscope including illumination light filters and observation light filters will be illustrated as an embodiment of an optical system for fluorescence observation below. However, embodiments of the optical system for fluorescence observation are not limited to surgical microscopes.

A surgical microscope shown in FIG. 1 comprises microscopy optics 3 including an objective lens 5 having an optical axis 7. An object 9 is arranged for inspection in an object plane of the objective lens 5. Light emanating from the object 9 is formed into an image side beam bundle 11 by the objective lens 5. Two zoom systems 12, 13 are arranged in the image side beam bundle 11 at a distance from the optical axis 7. The zoom systems 12, 13 supply partial beam bundles 14 and 15, respectively, of the image side beam bundle 11 to oculars 16 and 17 via deflecting prisms not shown in FIG. 1. A user may look with his left eye 18 and his right eye 19 into the oculars 16 and 17, respectively, in order to observe a magnified representation of the object 9 as an image.

A semitransparent mirror 21 is arranged in the partial beam bundle 15, for supplying a portion of the light of the beam bundle 15 as a beam 23 to a camera system 24. The camera system 24 may comprise one or more cameras. In the illustrated example, the camera system 24 comprises a camera 32 and a camera 55. Light of the beam 23 having traversed a semitransparent mirror 25 is supplied to the camera 32 via camera adapter optics 31. Light of the beam 23 reflected from the semitransparent mirror 25 is supplied to the camera 55 via a first observation light filter 57 and camera adapter optics 53.

The camera 55 is used for recording fluorescent light images. The camera 55 can be a color camera including an image sensor, comprising, for example, separate pixels for the colors red, green and blue. An example of such image sensor is a Bayer sensor. Moreover, the color camera can be of a type comprising plural monochrome image sensors, which are supplied with light of different wavelength ranges via a dichroic beam splitter.

The first observation light filter 57 can be inserted in and removed from the beam 29 by an actuator 59 which is controlled by a controller 35 as indicated schematically by a double arrow 58 in FIG. 1. The surgical microscope 1 offers two modes of operation for fluorescence observation. In a first mode of operation, the first observation light filter 57 is arranged in the beam 29 and, consequently, in a beam path between the object 9 and the camera 55, whereas the first observation light filter 57 is not arranged in this beam path in the second mode of operation.

In the first mode of operation, the first observation light filter 57 is arranged in the beam path between the object 9 and the camera 55, while no filter is arranged in the beam path between the object 9 and the ocular 17. Consequently, the user can observe with their eye 19 a normal light image of the object in the first mode of operation, whereas the camera 55 can detect fluorescent light images.

In the second mode of operation, a second observation light filter 96 is arranged in the beam path between the object 9 and the camera 55 and in the beam path between the object 9 and the ocular 17. The second observation light filter 96 can be inserted in and be removed from the beam path by an actuator 98 which is controlled by the controller 35 as indicated schematically by the double arrow 99 in FIG. 1. In the first mode of operation, the second observation light filter 96 is not arranged in the beam path between the object 9 and the ocular 17 and in the beam path between the object 9 and the camera 55. The second observation light filter 96 is arranged in the beam paths downstream of the beam splitter 21, so that the second observation light filter 96 is simultaneously arranged in both beam path between the object 9 and the ocular 17 and in the beam path between the object 9 and the camera 55. Consequently the user observes, via the ocular 17, in the second mode of operation a fluorescent light image which is also detected by the camera 55. It is also possible to arrange the second observation light filter 96 only in the beam path between the object and the camera 55 and not in the beam path between the object 9 and the ocular 17, for example, by a combined arrangement of the observation light filter 96 and the observation light filter 57 on a filter carrier, which is moved by the actuator 59 to alternatively arrange the first observation light filter 57 or the second observation light filter in the beam path between the object 9 and the camera 55.

The first observation light filter 57 is a fluorescent light filter which allows only fluorescent light from a fluorescence agent contained in the object 9 to traverse the first observation light filter 57. Consequently the camera 32 can detect a normal light image of the object 9, whereas the camera 55 detects a fluorescent light image of the object 9. Images of the cameras 32 and 55 are transmitted to the controller 35, via datalinks 33 and 65, respectively. The images can be processed by the controller 35 and stored in storage medium 95.

Similarly, a semitransparent mirror 37 can be arranged in the other partial beam bundle 14 in order to supply a beam 39 to a camera 43 via adapter optics 41. The camera 43 can also detect normal light images of the object 9, wherein the detected images are transmitted to the controller 35 via a data link 45.

A display 69 is connected to the controller via a data link 67, wherein a displayed image is projected into the beam path towards the ocular via an projection optics 70 and an semitransparent mirror 68 arranged in the partial beam bundle 15 so that the observer can observe both the image displayed by the display 69 and the direct image of the object 9. Thus, the controller 35 can project, for example, representations of data, images of the object as detected by the cameras 32, 55 and 43, or images generated by image processing of the detected images into the ocular 17.

The images detected by the cameras can also be transmitted by the controller 35 to a head mounted display 49, wherein the head mounted display 49 comprises two displays 51 and 52 for the right and left eye, respectively, of an observer.

According to the example shown in FIG. 1, the second observation light filter 96, the beam splitter 21 and the semitransparent mirror 68 are only arranged in the beam path between the object and the right ocular 17. The cameras 55 and 32 only receive light of the beam path directed to the ocular 17, accordingly. Also, the display 69 projects displayed images only into the beam path directed to the ocular 17. However it is also possible to provide suitable components also in the beam path between the object 9 and the left ocular 16, so that the arrangement of the surgical microscope 1 is symmetrical with respect to the beam paths directed to the oculars 16 and 17.

The surgical microscope 1 further comprises an illumination system 63 to generate an illumination light beam 81 directed towards the object 9. The illumination system 63 comprises a broad-band light source, such as a halogen lamp or a xenon lamp 71, a reflector 72, and a collimator 73 to generate a collimated light beam 74. The collimated light beam 74 is directed onto an end 76 of a fiber bundle 77 by one or more lenses 75, such that light emitted by the lamp 71 is coupled into the fiber bundle 77. The light is transmitted through the fiber bundle 77 and supplied to a location close to the object 9 where it is emitted from end 78 of the fiber bundle 77 and is collimated by collimating optics 79 to form an illumination light beam 81 directed towards the object.

The illumination system 63 further comprises a filter plate 83 which includes a first illumination light filter 84 for fluorescence observation, a second illumination light filter 82 for fluorescence illumination, and an illumination light filter 85 for normal light observation. An actuator 87 controlled by the controller is provided to selectively arrange the first illumination light filter 84 for fluorescence observation, the second illumination light filter 82 for fluorescence observation, or the illumination light filter 85 for normal light observation in the beam 74 as indicated by a double arrow 88. When a fluorescence is to be excited in the object 9, the first illumination light filter 84 for fluorescence observation or the second illumination light filter 82 for fluorescence observation is arranged in the beam 74, whereas the illumination light filter 85 for normal light observation is arranged in the beam 74 when the object 9 should be observed under illumination with normal light, such as white light. The illumination light filter 85 for normal light observation can be configured to block infrared light or near infrared light emitted from the lamp 71 in order to prevent an undesired warming of the object 9, whereas light of shorter wavelengths may traverse the illumination light filter 85 for normal light observation.

The selective arrangement of the first illumination light filter 84 for the fluorescence observation, of the second illumination light filter 82 for the fluorescence observation, and of the illumination light filter 85 for the normal light observation in the beam 74 can be controlled by the user via an input device, such as a switch 97 or a keyboard 98 connected to the controller 35. Further, the controller 35 can execute a program which changes the illumination light filter arranged in the beam path between the light source 71 and the object 9. The first illumination light filter 84 is arranged in the beam path between the light source 71 and the object 9 in the first mode of operation, wherein the first observation light filter 57 is arranged in the beam path between the object 9 and the camera 55 in this first mode of operation. The second illumination light filter 82 is arranged in the beam path between the light source 71 and the object 9 in the second mode of operation, wherein the second observation light filter 96 is arranged in the beam path between the object 9 and the camera 55 in this second mode of operation.

The transmission characteristics of the first illumination light filter 84 for fluorescence observation and of the first observation light filter 57 for the fluorescence observation will be illustrated with reference to FIG. 2 below.

Figure 2:
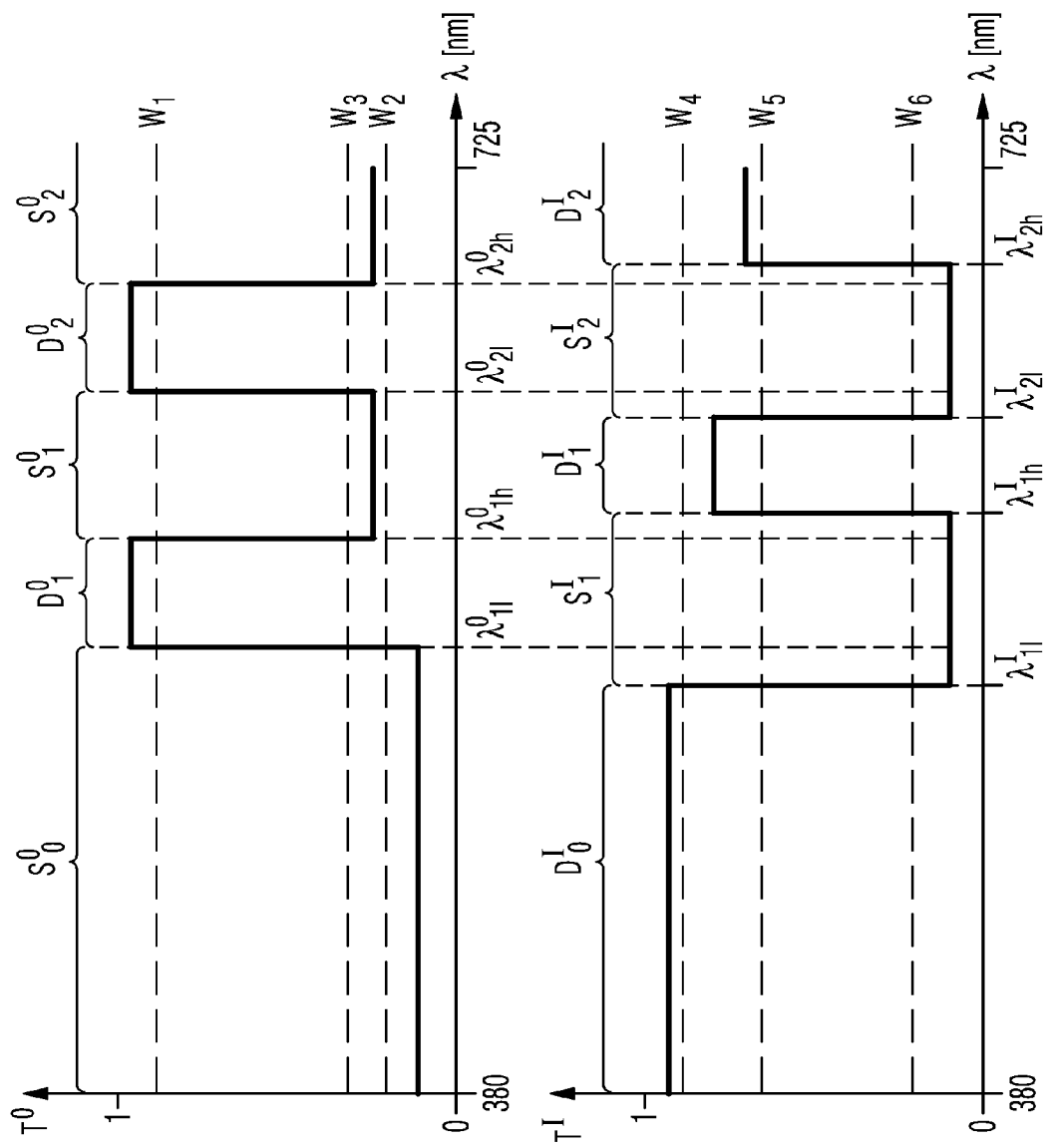
FIG. 2 is a schematic illustration of transmission characteristics of a first observation light filter and a first illumination light filter according to an embodiment and which can be used in a first mode of operation of the optical system for fluorescence observation of FIG. 1.

FIG. 2 schematically illustrates in its upper part transmission characteristics $T^O$ of the first observation light filter 57 and in its lower part the transmission characteristics $T^I$ of the first illumination light filter 84. In FIG. 2, elements of the first observation light filter 57 are labeled with the superscript O (observation) and elements of the first illumination light filter are denoted by the superscript I (illumination). The transmission characteristics are illustrated for the wavelength range 380 nm≤λ≤725 nm. In this wavelength range, both light filters 57, 84 have plural transmitting regions and blocking regions. The transmitting regions are denoted by the letter D, and the blocking regions are denoted by the letter S. The transmitting regions and the blocking regions are numbered in FIG. 2 from the left to the right, beginning with O, wherein subscripts represent the number of the transmitting and blocking regions, respectively.

The transmittance T is small in blocking regions, and the transmittance T is large in transmitting regions. In the illustration of FIG. 2, the transmittance changes abruptly at the edges between the transmitting regions and the blocking regions. This is an idealized behavior of light filters not found in practice where the transmittance changes steadily at the edges between blocking regions and transmitting regions. Wavelengths λ indicating the edges between the blocking and transmitting regions are denoted by a subscript in FIG. 2, wherein l (low) represents a left edge of a region and h (high) represents a right edge of a region.

The first observation light filter 57 should allow fluorescent light to traverse the first observation light filter 57. Therefore, the first observation light filter provides two transmitting regions $D_1^O$ and $D_2^O$. The transmission characteristics of the first transmitting region $D_1^O$ have a left edge at a wavelength $\lambda_{1l}^O$ and a right edge at a wavelength $\lambda_{1h}^O$. The second transmitting region $D_2^O$ has a left edge at a wavelength $\lambda_{2l}^O$ and a right edge at a wavelength $\lambda_{2h}^O$. The wavelengths $\lambda_{1l}^O$ and $\lambda_{2h}^O$ are selected such that they are within the fluorescence spectrum of the examined fluorescence, such that fluorescent light of a significant intensity is emitted in a wavelength range from $\lambda_{1l}^O$ to $\lambda_{2h}^O$. In the wavelength ranges outside of transmitting regions the, observation light filter provides blocking regions. These are one blocking region $S_0^O$ at wavelengths between 380 nm and $\lambda_{1l}^O$, a further blocking region $S_1^O$ at wavelengths between $\lambda_{1h}^O$ and $\lambda_{2l}^O$, and yet a further blocking region $S_2^O$ at wavelengths between $\lambda_{2h}^O$ and 725 nm.

Within each of the blocking regions and transmitting regions a mean transmittance $\overline{T}$ can be determined. For example, the mean transmittance $\overline{T}$ of the transmitting region $D_1^O$ can be calculated by the following formula:

$$\overline{T} = \frac{1}{\lambda_{1h}^O - \lambda_{1l}^O} \cdot \int_{\lambda_{1l}}^{\lambda_{1h}^O} T(\lambda)\,d\lambda$$

In each of the transmitting regions $D^O$, the mean transmittance $\overline{T}$ is greater than a value $W_1$ which can be, for example, greater than 0.7, greater than 0.8, or greater than 0.9. In the first blocking region $S_0^O$, the mean transmittance $\overline{T}$ is smaller than a value $W_2$, and in the further blocking regions $S_1^O$ and $S_2^O$, the mean transmittance $\overline{T}$ is smaller than a value $W_3$. In practice, the first blocking region $S_0^O$ is much wider than the further blocking regions $S_1^O$ and $S_2^O$, so that the value $W_3$ can be greater than the value $W_2$, without a significant amount of direct illumination light traversing the first observation light filter. Exemplary values for the values $W_2$ and $W_3$ are smaller than 0.3, smaller than 0.2 and smaller than 0.1.

Since light traversing the transmitting regions $D^O$ of the first observation light filter is substantially only fluorescent light, the first illumination light filter provides blocking regions at those wavelengths at which the first observation light filter has transmitting regions. The transmitting region $D_1^O$ of the first observation light filter corresponds to a blocking region $S_1^I$ of the first illumination light filter, and the transmitting region $D_2^O$ of the first observation light filter corresponds to a blocking region $S_2^I$ of the first illumination light filter. The blocking region $S_1^I$ is arranged between the wavelengths $\lambda_{1l}^I$ and $\lambda_{1h}^I$, and the blocking region $S_2^I$ is arranged between the wavelengths $\lambda_{2l}^I$ and $\lambda_{2h}^I$. To prevent illumination light to traverse both light filters, the blocking regions of the first illumination light filter are chosen wider than the transmitting regions of the first observation light filter. In particular the following relations are fulfilled $\lambda_{1l}^I < \lambda_{1l}^O$, $\lambda_{1h}^I > \lambda_{1h}^O$, $\lambda_{2l}^I < \lambda_{2l}^O$ and $\lambda_{2l}^I > \lambda_{2h}^O$.

The first illumination light filter has transmitting regions at those wavelengths at which it does not have a blocking region. These are a first transmitting region $D_0^I$ between 380 nm and $\lambda_{1l}^I$, a further transmitting region $D_1^I$ between $\lambda_{1h}^I$ and $\lambda_{2l}^I$, and yet a further transmitting region $D_2^I$ between $\lambda_{2h}^I$ and 725 nm. In the blocking regions, the mean transmittance is smaller than a value $W_6$, in the first transmitting region $D_0^I$, the mean transmittance is greater than a value $W_4$, and in each of the further transmitting regions $D_1^I$ and $D_2^I$, the mean transmittance is greater than a value $W_5$. Since the transmitting region $D_0^I$ has a greater width than the other transmitting regions $D_1^I$ and $D_2^I$ in practice, the value $W_4$ can be greater than the value $W_5$. For example, the values $W_4$ and $W_5$ can be greater than 0.7, greater than 0.8, or greater than 0.9. The value $W_6$ can be smaller than 0.3, smaller than 0.2, or smaller than 0.1.

The transmitting region $D_0^I$ is provided to illuminate the object for two different purposes. On the one hand, the light, traversing the first illumination light filter in the transmitting region $D_0^I$, excites the fluorescence, so that corresponding fluorescent light can traverse the transmitting regions $D_1^O$ and $D_2^O$ of the first observation light filter and reaches the camera 55. The camera 55 then detects a fluorescent light image of the object. On the other hand, the light traversing the first illumination light filter in the transmitting region $D_0^I$ provides a normal light illumination of the object, so that the user can directly observe the object with their eyes 18 and 19 via the oculars 16 and 17. Similarly, the camera 32 can detect a normal light image of the object.

If the object were illuminated only with light traversing the first illumination light filter in the transmitting region $D_0^I$, the object would appear with a heavily altered color impression, because important portions from the visible light spectrum are missing due to the blocking regions $S_1^I$ and $S_2^I$ of the first illumination light filter.

In conventional optical systems for fluorescence observation, an illumination light filter comprises only one blocking region, which would extend from $\lambda_{1l}^I$ to $\lambda_{2h}^I$ in the illustration of FIG. 2. In the present embodiment, two blocking regions $S_1^I$ and $S_2^I$, which are not overlapping and which are separated by the transmitting region $D_1^I$, are provided in the first illumination light filter. The first illumination light filter has a purpose of illuminating the object with light for normal light illumination. With a suitably selected transmitting region $D_1^I$, the color impression of the object can be significantly improved, and a white object can appear nearly white. The transmitting region $D_1^I$ offers an essential advantage to the improvement of the color impression of the observed object under normal light. The transmitting region $D_1^I$ has a consequence that the first observation light filter for fluorescence observation has to provide the corresponding blocking region $S_1^O$ at those wavelengths where the illumination light filter has the transmitting region $D_1^I$. The blocking region $S_1^O$ of the first observation light filter reduces the amount of detectable fluorescent light. However, the advantage of the improved color impression for normal light observation is achieved. Also, the further transmitting region $D_2^I$ is provided for illuminating the object with even more wavelengths in order to further improve the color impression for normal light observation.

Light filter systems using these principles can be varied from the foregoing description, which was provided for illustrating the principles of the light filter system for the first mode of operation for fluorescence observation with reference to the schematic illustration of FIG. 2. Various modifications of the filter system are conceivable. For example, the transmitting region $D_2^I$ can be omitted, so that the blocking region $S_2^I$ to the wavelength 725 nm. Furthermore, the number of transmitting regions $D_1^O$, $D_2^O$ can be increased, which results in an increased number of transmitting regions $D_1^I$, $D_2^I$, . . . of the first illumination light filter corresponding to the higher number of blocking regions $S_1^O$, $S_2^O$, . . . of the observation light filter.

An embodiment of an optical filter system having a first illumination light filter for fluorescence observation and a first observation light filter for fluorescence observation adapted to the observation of a fluorescence of Protoporphyrine IX in the first observation mode will be illustrated below. The fluorescence of Protoporphyrine IX can be used to visualize gliomas. A patient is administered with 5-ALA before a surgery, resulting in the desired fluorescence of Protoporphyrine IX several hours later.

Figure 3:
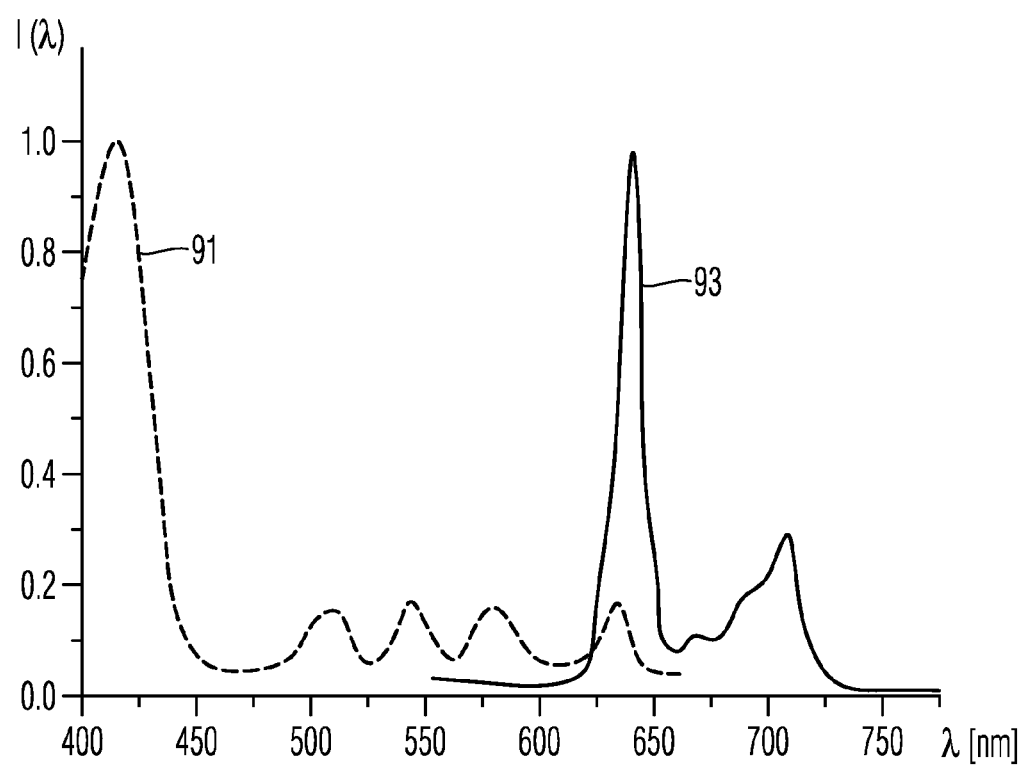
FIG. 3 is a graph showing an excitation spectrum and a fluorescence spectrum of Protoporphyrine IX.

The fluorescence of Protoporphyrine IX is shown in FIG. 3 for wavelengths from 400 nm to 775 nm. The intensity $I(\lambda)$ of the excitation spectrum of Protoporphyrine IX in dependence of the wavelength $\lambda$ is depicted by a broken line 91, and the intensity $I(\lambda)$ of the emission spectrum of Protoporphyrine IX in dependence of the wavelength is depicted by a full line 93. The maxima of both spectra are normalized to 1.0.

Figure 4:
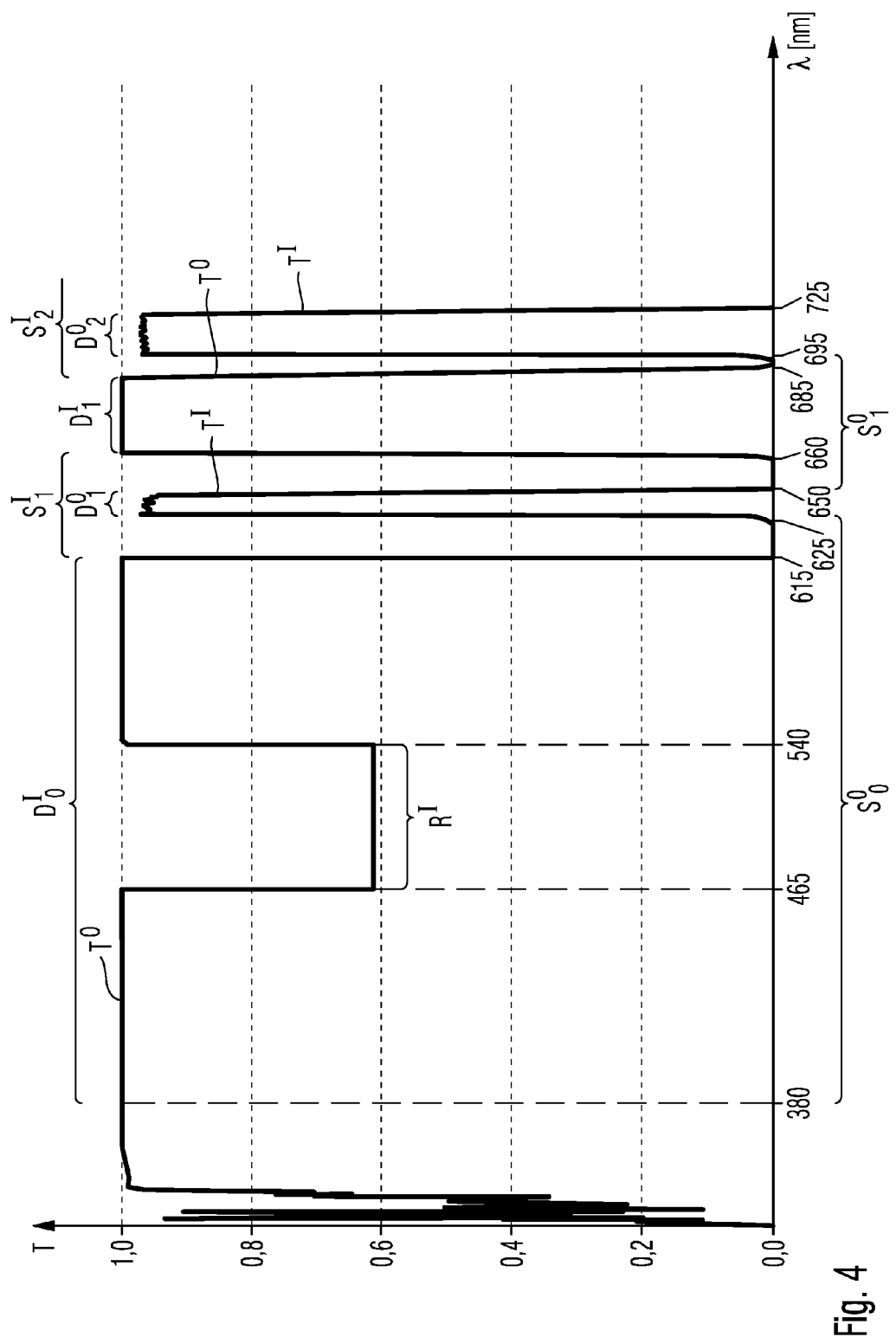
FIG. 4 is a graph showing transmission characteristics of a first observation light filter and a first illumination light filter adapted to the fluorescence of Protoporphyrine IX.

FIG. 4 shows a graph of transmission characteristics of a light filter system which is adapted to the observation of the fluorescence of Protoporphyrine IX for the fluorescence observation in the first mode of operation. In contrast to FIG. 2, where the transmittance of the first illumination light filter was illustrated in the lower part of the figure and the transmittance of the first observation light filter was illustrated in the upper part of the figure, the transmission characteristics $T^I$ of the first illumination light filter and the transmission characteristics $T^O$ of the first observation light filter of this light filter system are illustrated in a common graph in FIG. 4. The relations for the transmitting regions and the blocking regions of the particular transmission characteristics correspond to those of FIG. 2.

The first observation light filter comprises blocking regions $S_0^O$ and $S_1^O$ and transmitting regions $D_1^O$ and $D_2^O$.

The blocking region $S_0^O$ is arranged within a wavelength range 380 nm$<\lambda<\lambda_{1l}^O$, as to $\lambda_{1l}^O$=625 nm.

The transmitting region $D_1^O$ is arranged within a wavelength range $\lambda_{1l}^O<\lambda<\lambda_{1h}^O$, as to $\lambda_{1h}^O$=650 nm.

The blocking region $S_1^O$ is arranged within a wavelength range $\lambda_{1h}^O<\lambda<\lambda_{2l}^O$, as to $\lambda_{2l}^O$=695 nm.

The transmitting region $D_2^O$ is arranged within a wavelength range $\lambda_{2l}^O<\lambda<725$ nm.

The first illumination light filter comprises transmitting regions $D_0^I$ and $D_1^I$ as well as blocking regions $S_1^I$ and $S_2^I$.

The transmitting region $D_0^I$ is arranged within a wavelength range 380 nm$<\lambda<\lambda_{1l}^I$ as to $\lambda_{1l}^I$=615 nm.

The blocking region $S_1^I$ is arranged within a wavelength range $\lambda_{1l}^I<\lambda<\lambda_{1h}^I$, as to $\lambda_{1h}^I$=660 nm.

The transmitting region $D_1^I$ is arranged within a wavelength range $\lambda_{1h}^I<\lambda<\lambda_{2l}^I$, as to $\lambda_{2l}^I$=685 nm.

The blocking region $S_2^I$ is arranged within a wavelength range $\lambda_{2l}^I<\lambda<725$ nm.

The first illumination light filter further comprises a region $R^I$ between 465 nm and 540 nm within the transmitting region $D_0^I$, where the transmittance is reduced to a value of about 0.62. Thereby the amount of green light reaching the object is reduced, which results in a further improvement of the color impression of the object during normal light observation.

Figure 5:
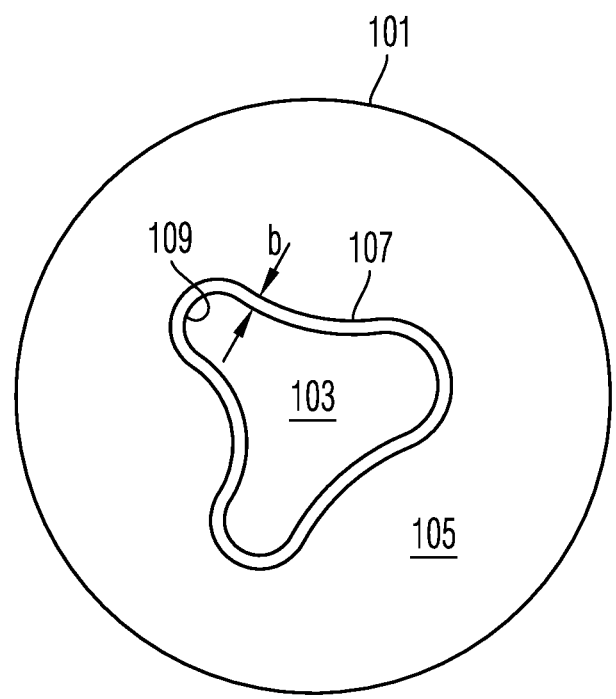
FIG. 5 is a schematic illustration of an image which can be seen by looking into an ocular of the optical system for fluorescence observation shown in FIG. 1 in a first mode of operation for fluorescence observation.

FIG. 5 is an exemplary schematic illustration of an image 101 of the object 9 as it could be seen by with the eye 19 using the ocular 17 in the first mode of operation for fluorescence observation. It is assumed that the imaged region of the object 9 contained in the image 101 includes a fluorescent region 103 and a surrounding non-fluorescent region 105. The fluorescent region 103 can be identified in the fluorescence image obtained in the first mode of operation by performing an image analysis using the controller 35. The fluorescent region 103 is not or nearly not observable by the naked eye in the normal light image generated via the beam path from the object 9 to the ocular 17. Because of that, the controller 35 identifies the fluorescent region 103 by image processing of the fluorescent light image and generates a representation of the boundary 107 of the fluorescent region 103. The controller generates an image, based on the representation of the boundary 107 of the fluorescent region, which is then transmitted to the display 69. The display 69 displays and projects the generated image into the ocular 17, so that the eye 19 can observe both the normal light of the object 9 and the superposed image. The boundary 107 of the fluorescent region 103 is well visible as an overlay on the normal light image. For example, the representation of the boundary 107 of the fluorescent region 103 can comprise a line 109 with a width b, which extends along the boundary 107 of the fluorescent region 103. Thereby the width b is substantially smaller than a lateral extension of the fluorescent region 103, so that the line 109, which represents the boundary 107 in the image 101, occupies a relative small portion of the image and does not cover a major amount of the fluorescent region 103. As a consequence, the boundary 107 of the fluorescent region 103 can be well identified in the image 101, and the fluorescent region 103 as well as the surrounding non-fluorescent region 105 can be observed under a substantially unaltered natural color impression of a normal light image. When the fluorescent region 103 of the object 9 is tumor tissue in which fluorescent agent has accumulated, such tumor tissue can be accurately removed during observation of the normal light image, by using the representation 109 of the boundary 107 of the fluorescent region 103 for orientation.

In order to identify the fluorescent regions 103 within the fluorescent light image, a decision is made for every single pixel of the fluorescent light image whether this pixel is part of a fluorescent region or not. This can be performed based on the intensity of the pixel of the fluorescent light image, for example. The intensity of the pixel can be compared with a threshold value set in advance. If the intensity exceeds the threshold, it is decided that the pixel is part of the fluorescent region, and, if the intensity is below the threshold, it is decided that the pixel is not part of the fluorescent region. Thus, the threshold set in advance is a decision parameter of the image processing.

Other decision parameters are possible. For example, a gradient of the intensity can be used as a decision parameter since changes of the intensity are greater at the boundaries of fluorescent regions than in the interior or exterior of the fluorescent regions.

It is apparent that the position and the extent of identified fluorescent regions in a fluorescence image are dependent on the selection of the decision parameter. Therefore it is possible to modify or edit the decision parameter by input via the keyboard 98, for example. Hence it is desirable to adjust the decision parameter, until the representation 109 of the boundary 107 of the fluorescent region 103 coincides with real borders between the fluorescent regions and the non-fluorescent regions of the object. In the present embodiment, an option is provided for setting of the decision parameter and for calibrating the image processing in the first mode of operation. An alternative fluorescence observation, using a different optical filter system, is performed in a second mode of operation. In the second mode of operation, the second illumination light filter 82 for fluorescence observation and the second observation light filter 96 for the fluorescence observation are arranged in the beam paths.

Figure 6:
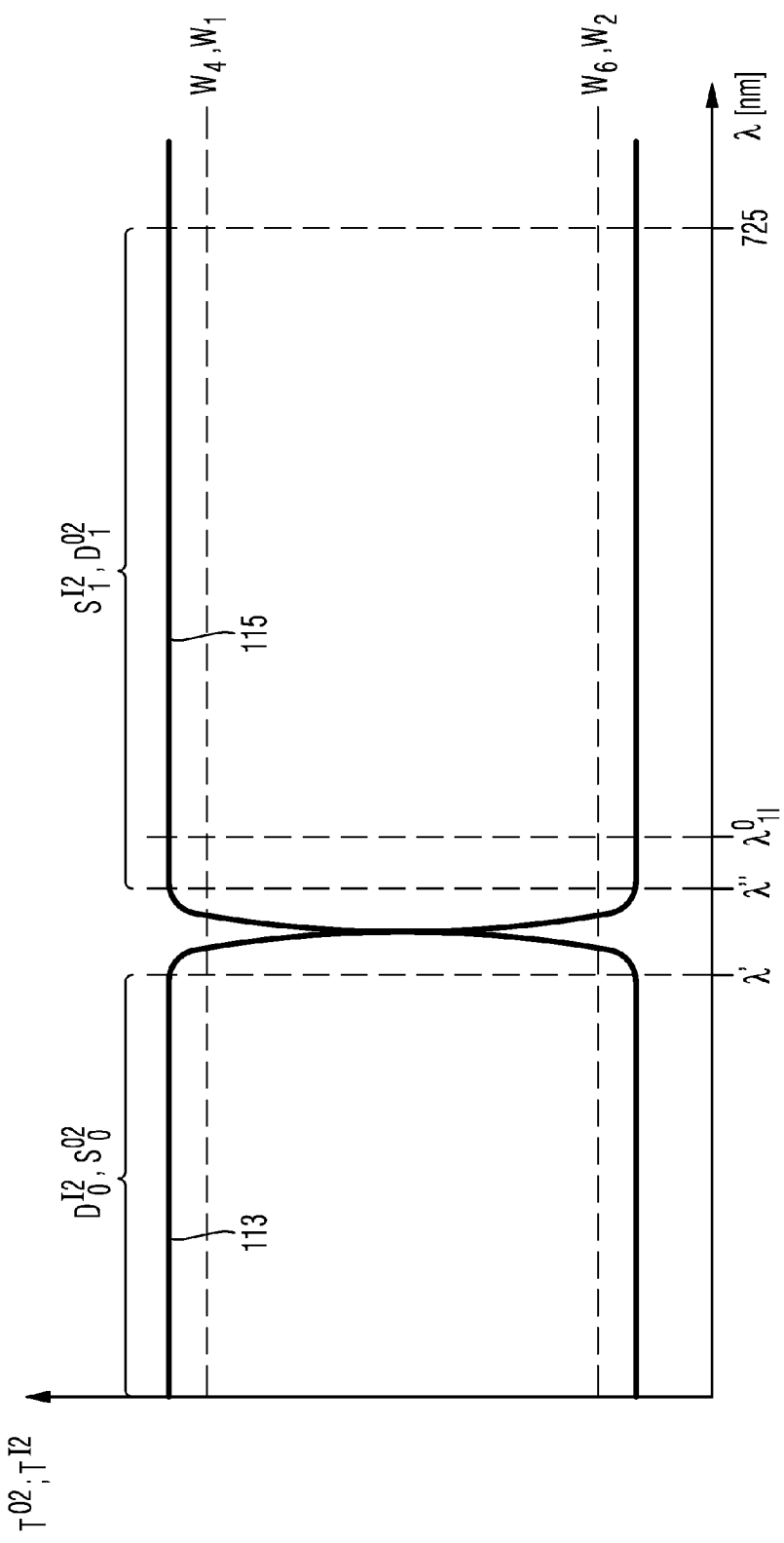
FIG. 6 is a schematic illustration of transmission characteristics of a second observation light filter and a second illumination light filter according to an embodiment which can be used in a second mode of operation of the optical system for fluorescence observation shown in FIG. 1.

In the following, transmission characteristics of the second illumination light filter 82 and of the second observation light filter 96 are described with reference to FIG. 6. In FIG. 6, a line 113 represents the transmittance $T^{I2}$ of the second illumination light filter 82 in dependence of the wavelength, and a line 115 represents the transmittance $T^{O2}$ of the second observation light filter 96 in dependency of the wavelength. The second illumination light filter comprises a transmitting region $D_0^{I2}$ between 380 nm and a wavelength $\lambda'$. Further the second illumination light filter comprises a blocking region $S_1^{I2}$ between the wavelength $\lambda''$ and 725 nm. The wavelengths $\lambda'$ and $\lambda''$ are both smaller than the smallest wavelength $\lambda_{1l}^O$ of the first wavelengths of the transmitting regions of the observation light filter 84 (cf. FIG. 2). The wavelength $\lambda''$ is greater than the wavelength $\lambda'$, and a difference between the wavelengths $\lambda''$ and $\lambda'$ can, for example, be 50 nm. Between the wavelength $\lambda'$ and the wavelength λ" the transmittance of the second illumination light filter decreases continuously.

A blocking region $S_0^{O2}$ of the second observation light filter extends from 380 nm to the wavelength λ', and a transmitting region $D_1^{O2}$ of the second observation light filter extends from the wavelength λ" to 725 nm. Between the wavelength λ' and the wavelength λ" the transmittance of the second observation light filter 96 increases continuously.

Within the transmitting regions $D_O^{I2}$ and $D_1^{O2}$, the transmittances are greater than the values $W_1$ and $W_4$ according to FIG. 2, and in the blocking regions $S_1^{I2}$ and $S_0^{O2}$ the transmittances are smaller than the values $W_2$ and $W_6$ according to FIG. 2.

Within the wavelength range between λ' and λ", the product of the transmittances of the two light filters is greater than 0.05, for example, which allows light, which is not fluorescent light, to reach the eye 19, or the camera 55. Moreover, also fluorescent light reaches the eye 19, or the camera 55, so the light from the wavelength ranges between λ' and λ" and the fluorescent light are added at the eye, or camera, resulting in a mixed color. It can be determined whether each given location in the image lies within a fluorescent region, within a non-fluorescent region, or on the boundary of a fluorescent region based on the color of the image at the given location.

Such method has already been proposed for the identification of boundaries of tumors, and especially of brain tumors, based on the fluorescence agent Protoporphyrine IX. The identification of boundaries of fluorescent regions and the subsequent generated representation of boundaries of fluorescent regions is illustrated US 2013/0307953 A1, the disclosure of which is hereby included by reference in this application in its entirety.

In the illustrated modes of operation of the surgical microscope 1, a switching is performed between the first mode of operation and the second mode of operation. In the second mode of operation, the boundaries of fluorescent regions are identified based on their color, and the decision parameter of the image processing of the first mode of operation is modified until the identified boundaries of the fluorescent regions in the first mode of operation substantially coincide with the identified boundaries of the fluorescent regions the second mode of operation. When the decision parameter has been adjusted accordingly, the fluorescence observation can be continued in the first mode of operation, because during this mode of operation, fluorescent regions and non-fluorescent regions can be observed under an almost unaltered natural color impression, and the boundaries of the fluorescent regions are visualized in the image.

The present application discloses, amongst others, the following characteristics setups:

(1) An optical light filter system for a fluorescence observation, wherein the light filter system comprises an illumination light filter (I) and an observation light filter (O); wherein the first observation light filter (O) has, in a wavelength range from 380 nm to 725 nm, a transmission characteristic as follows:
at least two non-overlapping transmitting regions ($D_1^O$, $D_2^O$) of the observation light filter (O), each of the transmitting regions having, between a first wavelength ($\lambda_{1l}^O$, $\lambda_{2l}^O$) and a second wavelength ($\lambda_{1h}^O$, $\lambda_{2h}^O$), a mean transmittance greater than a first value ($W_1$); and
plural blocking regions ($S_0^O$, $S_1^O$), whose number coincide with the number of transmitting regions ($D_1^O$, $D_2^O$), of the observation light filter (O), the plural blocking regions including: a first blocking region ($S_0^O$) of the observation light filter (O) having, between 380 nm and a smallest ($\lambda_{1l}^O$) of the first wavelengths ($\lambda_{1l}^O$, $\lambda_{2l}^O$) of the at least two transmitting regions ($D_1^O$, $D_2^O$) of the observation light filter (O), a mean transmittance smaller than a second value ($W_2$); and
at least one further blocking region ($S_1^O$) of the observation light filter (O), each of the further blocking regions ($S_1^O$) having, between the second wavelength ($\lambda_{1h}^O$) of one ($D_1^O$) of the at least two transmitting regions of the observation light filter and the first wavelength ($\lambda_{2l}^O$) of a further one ($D_2^O$) of the at least two transmitting regions ($D_1^O$, $D_2^O$) of the first observation light filter (O), a mean transmittance smaller than a third value ($W_3$);
wherein the first illumination light filter (I) has, in a wavelength range from 380 nm to 725 nm, a transmission characteristic as follows:
plural transmitting regions ($D_0^I$, $D_1^I$) of the illumination light filter (I), the plural transmitting regions including:
a first transmitting region ($D_0^I$) of the illumination light filter (I) having, between 380 nm and a wavelength ($\lambda_{1l}^I$) smaller than the smallest ($\lambda_{1l}^O$) of the first wavelengths ($\lambda_{1l}^O$, $\lambda_{2l}^O$) of the at least two transmitting region ($D_1^O$, $D_2^O$) of the observation light filter (O), a mean transmittance greater than a fourth value ($W_4$); and
further transmitting regions ($D_1^I$) of the illumination light filter (I), each of the further transmitting regions ($D_1^I$) having, between a wavelength ($\lambda_{1h}^I$) greater than the second wavelength ($\lambda_{1h}^O$) of a transmitting region) ($D_1^O$ of the first observation light filter (O), and a wavelength ($\lambda_{2l}^I$) smaller than the first wavelength ($\lambda_{2l}^O$) of a further one transmitting region ($D_2^O$) of the observation light filter (O), a transmittance greater than a fifth value ($W_5$); and
plural blocking regions ($S_1^I$, $S_2^I$) of the illumination light filter (I), each of the blocking regions ($S_1^I$, $S_2^I$) of the illumination light filter (I) having, between the wavelength ($\lambda_{1l}^I$, $\lambda_{2l}^I$) smaller than the first wavelength ($\lambda_{1l}^O$, $\lambda_{2l}^O$) of one of the transmitting regions ($D_1^O$, $D_2^O$) of the first observation light filter (O), and the wavelength ($\lambda_{1h}^I$, $\lambda_{2h}^I$) greater than the second wavelength ($\lambda_{1h}^O$, $\lambda_{2h}^O$) of this transmitting region ($D_1^O$, $D_2^O$) of the observation light filter (O), a mean transmittance smaller than a sixth value ($W_6$).

(2) The optical light filter system according to setup (1), wherein the first value ($W_1$) is greater than 0.7, particularly greater than 0.8 and particularly greater than 0.9.

(3) The optical light filter system according to setup (1) or (2), wherein the second value ($W_2$) is smaller than 0.3, particularly smaller than 0.2 and particularly smaller than 0.1.

(4) The optical light filter system according to one of the setups (1) to (3), wherein the third value ($W_3$) is smaller than 0.3, particularly smaller than 0.2 and particularly smaller than 0.1.

(5) The optical light filter system according to one of the setups (1) to (4), wherein the second value ($W_2$) is smaller than the third value ($W_3$), particularly the second value ($W_2$) is two times smaller than the third value ($W_3$), and particularly the second value ($W_2$) is five times smaller than the value ($W_3$).

(6) The optical light filter system according to one of the setups (1) to (5), wherein the fourth value ($W_4$) and/or the fifth value ($W_5$) are greater than 0.7, particularly greater than 0.8 and particularly greater than 0.9.

(7) The optical light filter system according to one of the setups (1) to (6), wherein the sixth value ($W_6$) is smaller than 0.3, particularly smaller than 0.2 and particularly smaller than 0.1.

(8) The optical light filter system according to one of the setups (1) to (7), wherein the following formula is fulfilled:

$$\frac{1}{345\ nm}\int_{380\,nm}^{725\,nm} T^O(\lambda) \cdot T^I(\gamma)\,d\lambda < 0.01,$$

wherein $T^O(\lambda)$ is the transmittance of the observation light filter in dependency of the wavelength $\lambda$ and $T^I(\lambda)$ is the transmittance of the illumination light filter in dependency of the wavelength $\lambda$.

(9) The optical light filter system according to one of the setups (1) to (8), wherein the number of the transmitting regions ($D_1^O, D_2^O$) of the observation light filter counts two.

(10) The optical light filter system according to one of the setups (1) to (9), wherein the following relation is fulfilled:

610 nm≤$\lambda_{1l}^O$≤640 nm, particularly 620 nm≤$\lambda_{1l}^O$≤630 nm, wherein $\lambda_{1l}^O$ is the first wavelength of a first of at least two transmitting regions.

(11) The optical light filter system according to one of the setups (1) to (10), wherein the following relation is fulfilled:

630 nm≤$\lambda_{1h}^O$≤670 nm, particularly 640 nm≤$\lambda_{1h}^O$≤660 nm, wherein $\lambda_{1h}^O$ is the second wavelength of a first of at least two transmitting regions.

(12) The optical light filter system according to one of the setups (1) to (11), wherein the following relation is fulfilled:

10 nm≤$\lambda_{1h}^O - \lambda_{1l}^O$≤60 nm, particularly 20 nm≤$\lambda_{1h}^O - \lambda_{1l}^O$≤40 nm, wherein $\lambda_{1h}^O$ is the first wavelength and $\lambda_{1h}^O$ is the second wavelength of a first of at least two transmitting regions.

(13) The optical light filter system according to one of the setups (1) to (12), wherein the following relation is fulfilled:

680 nm≤$\lambda_{2l}^O$≤710 nm, particularly 690 nm≤$\lambda_{2l}^O$≤700 nm, wherein $\lambda_{2l}^O$ is the first wavelength of a second of at least two transmitting regions.

(14) The optical light filter system according to one of the setups (1) to (13), wherein the following relation is fulfilled:

10 nm≤$\lambda_{2h}^O - \lambda_{2l}^O$≤60 nm, particularly 20 nm≤$\lambda_{2h}^O - \lambda_{2l}^O$≤40 nm, wherein $\lambda_{2l}^O$ is the first wavelength and $\lambda_{2h}^O$ is the second wavelength of a second of at least two transmitting regions.

(15) The optical light filter system according to one of the setups (1) to (14), wherein the illumination light filter has a transmitting region within a wavelength range ($R^I$) between 440 nm and 560 nm, particularly between 465 nm and 540 nm, and the transmitting region having a width greater than 45 nm, wherein the illumination light filter has a transmittance less than 0.8, particularly less than 0.7, and particularly less than 0.65, within this wavelength range.

(16) The optical light filter system according to setup (15), wherein the width of the wavelength range is greater than 60 nm.

(17) A fluorescence observation system, comprising:
a light source configured to generate a light beam for illuminating an object region including a fluorescent agent;
a first camera configured to detect a fluorescent light image of the object region; and
an optical light filter system comprising an observation light filter (O) and an illumination light filter (I), wherein the illumination light filter (I) is arranged in a beam path between the light source and the object region, wherein the observation light filter (O) is arranged in a beam path between the object region and the first camera, and
wherein the optical light filter system is equal to one of the setups (1) to (16).

(18) The fluorescence observation system according to setup (17), further comprising a second camera for detecting a normal-light image of the object region.

(19) The fluorescence observation system according to setup (18), further comprising a first display, configured to display the fluorescent light image detected by the first camera and the normal light image, detected by the second camera, such that the fluorescent light image and the normal light image are superposed with each other.

(20) The fluorescence observation system according to one of the setups (17) to (19),
further comprising imaging optics configured to image the object region, wherein the imaging optics in particular comprises an ocular.

(21) The fluorescence observation system according to setup (20), further comprising a second display configured to project the fluorescent light image, detected by the first camera, in a beam path of the imaging optics.

(22) A method of usage of the optical light filter system according to one of the setups (1) to (16) and/or of the fluorescence observation system according to one of the setups (17) to (21), wherein the fluorescent agent includes Protoporphyrine IX.

While the disclosure has been described with respect to certain exemplary embodiments thereof, it is evident that many alternatives, modifications and variations will be apparent to those skilled in the art. Accordingly, the exemplary embodiments of the disclosure set forth herein are intended to be illustrative and not limiting in any way. Various changes may be made without departing from the spirit and scope of the present disclosure as defined in the following claims.

The invention claimed is:

1. An optical system for fluorescence observation, comprising:
optics including an ocular, a camera, a display, a light source, a first illumination light filter, a first observation light filter, and a controller;
wherein the optics provides a first beam path from the light source to an object region for illuminating the object region,
wherein the optics provides a second beam path from the object region to the ocular for imaging the object region via the ocular, wherein the optics provides a third beam path from the object region to the camera for imaging the object region onto the camera, and wherein the optics provides a fourth beam path from the display to the ocular for imaging an image, displayed by the display, via the ocular;

wherein the optical system has a first mode of operation, in which the first illumination light filter is arranged in the first beam path and the first observation light filter is arranged in the third beam path;

wherein the first observation light filter has, in a wavelength range from 380 nm to 725 nm, a transmission characteristics as follows:

at least two non-overlapping transmitting regions of the first observation light filter, each of the transmitting regions having, between a first wavelength and a second wavelength, a mean transmittance greater than a first value; and plural blocking regions of the first observation light filter, the plural blocking regions including: a first blocking region of the first observation light filter having, between 380 nm and a smallest one of the first wavelengths of the at least two transmitting regions of the first observation light filter, a mean transmittance smaller than a second value, and at least one further blocking region of the first observation light filter, each of the further blocking regions having, between the second wavelength of one of the at least two transmitting regions of the observation light filter and the first wavelength of a further one of the at least two transmitting regions of the first observation light filter, a mean transmittance smaller than a third value;

wherein the first illumination light filter has, in a wavelength range from 380 nm to 725 nm, a transmission characteristics as follows:

plural transmitting regions of the first illumination light filter, the plural transmitting regions including:

a first transmitting region of the first illumination light filter having, between 380 nm and a wavelength smaller than the smallest one of the first wavelengths of the at least two transmitting regions of the first observation light filter, a mean transmittance greater than a fourth value, and further transmitting regions of the first illumination light filter, each of the further transmitting regions having, between a wavelength greater than the second wavelength of a transmitting region of the first observation light filter and a wavelength smaller than the first wavelength of a further transmitting region of the observation light filter, a mean transmittance greater than a fifth value; and plural blocking regions of the first illumination light filter, each of the blocking regions of the first illumination light filter having, between the wavelength smaller than the first wavelength of one of the transmitting regions of the first observation light filter and the wavelength greater than the second wavelength of this transmitting region of the first observation light filter, a mean transmittance smaller than a sixth value;

wherein the controller is configured to process a fluorescent light image obtained by the camera in the first mode of operation by identifying a contiguous fluorescent region in the fluorescent light image obtained in the first mode of operation based on at least one decision parameter, generating a representation of a boundary of the contiguous fluorescent region, generating an image including the representation of the boundary of the contiguous fluorescent region, and supplying the generated image to the display.

2. The optical system according to claim 1, further comprising an input device for editing the at least one decision parameter.

3. The optical system according to claim 1, wherein the optics further comprises a second illumination light filter and a second observation light filter; and wherein the optical system has a second mode of operation, in which the second illumination light filter is arranged in the first beam path and the second observation light filter is arranged in the third beam path;

wherein the second illumination light filter has, in a wavelength range from 380 nm to 725 nm, a transmission characteristics as follows:

a transmitting region of the second illumination light filter having, between 380 nm and a first wavelength smaller than the smallest of the wavelengths of the at least two transmitting regions of the first observation light filter, a mean transmittance greater than the fourth value; and a blocking region of the second illumination light filter having, between a second wavelength greater than the first wavelength and smaller than the smallest of the first wavelengths of the at least two transmitting regions of the first observation light filter and 725 nm, a mean transmittance smaller than the sixth value;

wherein the second observation light filter has, in the wavelength range from 380 nm to 725 nm, a transmission characteristics as follows:

a blocking region of the second observation light filter having, between 380 nm and the first wavelength, a mean transmittance smaller than the second value; and a transmitting region of the second observation light filter having, between the second wavelength and 725 nm, a mean transmittance greater than the first value;

wherein the following formula is fulfilled in only one wavelength range:

$$T^{O2}(\lambda) \cdot T^{I2}(\lambda) \geq 0.05$$

and wherein the following formula is fulfilled for all other wavelengths outside that wavelength range:

$$T^{O2}(\lambda) \cdot T^{I2}(\lambda) < 0.05$$

wherein the wavelength range extends between the first wavelength and the second wavelength, and the wavelength range extends over more than 50 nm, and wherein $T^{O2}(\lambda)$ is the transmittance of the second observation light filter in dependence of the wavelength and $T^{I2}(\lambda)$ is the transmittance of the second illumination light filter in dependence of the wavelength.

4. The optical system according to claim 3, wherein the camera is a color camera and the controller is configured to switch the optical system from the first mode of operation to the second mode of operation;

to process a fluorescence image, obtained by the camera in the second mode of operation by identifying a boundary of a contiguous fluorescent region based on color information of the fluorescent light image obtained in the second mode of operation;

to switch the optical system from the second mode of operation to the first mode of operation, to determine the at least one decision parameter such that the boundary of the fluorescent region identified in the fluorescent light image obtained in the first mode of operation substantially coincides with the boundary of the fluorescent region identified in the fluorescent light image obtained in the first mode of operation.

5. The optical system according to claim 3, wherein the second observation light filter is arranged in the second beam path in the second mode of operation.

6. The optical system according to claim 3, wherein the second illumination light filter and the second observation light filter are configured for excitation and detection of a fluorescence of Protoporphyrine IX.

7. The optical system according to claim 1, wherein the first illumination light filter and the first observation light filter are configured for excitation and detection of a fluorescence of Protoporphyrine IX.

* * * * *

UNITED STATES PATENT AND TRADEMARK OFFICE
CERTIFICATE OF CORRECTION

PATENT NO. : 10,054,775 B2
APPLICATION NO. : 14/940639
DATED : August 21, 2018
INVENTOR(S) : Hauger et al.

Page 1 of 1

It is certified that error appears in the above-identified patent and that said Letters Patent is hereby corrected as shown below:

In the Specification

In Column 1, Line 32, delete "in the a" and insert -- in a --, therefor.

In Column 3, Line 2, delete "respective and" and insert -- respective region and --, therefor.

In Column 4, Line 25, delete "since of not" and insert -- since not --, therefor.

In Column 11, Line 7, delete "and an" and insert -- and a --, therefor.

In Column 12, Line 65, delete "the," and insert -- the --, therefor.

In Column 13, Line 43, delete "and $\lambda^I_{2l}$" and insert -- and $\lambda^I_{2h}$ --, therefor.

In Column 14, Line 45, delete "$S^I_2$ to" and insert -- $S^I_2$ extends to --, therefor.

In Column 17, Line 32, delete "illustrated US" and insert -- illustrated in US --, therefor.

In Column 17, Line 44, delete "regions the" and insert -- regions of the --, therefor.

In Column 18, Lines 31 and 32, delete "region) ($D^O_1$)" and insert -- region ($D^O_1$) --, therefor.

In Column 19, Line 10, delete "$\frac{1}{345\,nm}\int_{380\,nm}^{725\,nm} T^O(\lambda)\cdot T^I(\gamma)\,d\lambda < 0,01$" and insert -- $\frac{1}{345\,nm}\int_{380\,nm}^{725\,nm} T^O(\lambda)\cdot T^I(\lambda)\,d\lambda < 0,01$ --, therefor.

Signed and Sealed this
Twenty-third Day of October, 2018

Andrei Iancu
*Director of the United States Patent and Trademark Office*